(12) United States Patent
Green et al.

(10) Patent No.: US 10,242,851 B2
(45) Date of Patent: Mar. 26, 2019

(54) USING THEORETICAL COLLISION CROSS SECTION ("CCS") IN SAMPLE IDENTIFICATION

(71) Applicant: Micromass UK Limited, Wilmslow (GB)

(72) Inventors: Martin Raymond Green, Bowdon (GB); Kevin Giles, Stockport (GB); Keith Richardson, Derbyshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 358 days.

(21) Appl. No.: 15/125,328

(22) PCT Filed: Mar. 10, 2015

(86) PCT No.: PCT/GB2015/050702
§ 371 (c)(1),
(2) Date: Feb. 3, 2017

(87) PCT Pub. No.: WO2015/136273
PCT Pub. Date: Sep. 17, 2015

(65) Prior Publication Data
US 2017/0076927 A1      Mar. 16, 2017

(30) Foreign Application Priority Data

Mar. 10, 2014  (EP) ..................................... 14158643
Mar. 10, 2014  (GB) .................................. 1404195.8

(51) Int. Cl.
*H01J 49/00*   (2006.01)
*G01N 27/62*   (2006.01)

(52) U.S. Cl.
CPC ........ *H01J 49/0036* (2013.01); *G01N 27/622* (2013.01); *H01J 49/004* (2013.01); *H01J 49/005* (2013.01); *H01J 49/0031* (2013.01)

(58) Field of Classification Search
USPC .................................................. 250/281, 282
See application file for complete search history.

(56) References Cited

U.S. PATENT DOCUMENTS 6,495,824 B1   12/2002  Atkinson
7,812,305 B2   10/2010  Miller et al.
(Continued)

FOREIGN PATENT DOCUMENTS

GB      2393849     4/2006
GB      2490792     11/2012
(Continued)

OTHER PUBLICATIONS

Dwivedi et al., "Rapid Resolution of Carbohydrate Isomers by Electrospray Ionization Ambient Pressure Ion Mobility Spectrometry-Time-of-Flight Mass Spectrometry (ESI-APIMS-TOFMS)", Focus: From Mobilities to Proteomes, p. 1163-1175, Apr. 2007.
(Continued)

*Primary Examiner* — Kiet T Nguyen

(57) ABSTRACT

A method of mass spectrometry is disclosed that comprises predicting 1 one or more first reaction products which may result from subjecting an analyte to one or more reactions of interest, calculating 2 one or more first masses or mass to charge ratios and one or more first ion mobility values, collision cross sections or interaction cross sections of at least some first reaction product ions which may be generated from the one or more first reaction products under first conditions, and calculating one or more second masses or mass to charge ratios and one or more second ion mobility values, collision cross sections or interaction cross sections of at least some second reaction product ions which may be
(Continued)

generated from the one or more first reaction products under second different conditions. The method further comprises generating third ions from a sample under the first conditions, generating fourth ions from the sample under the second conditions, experimentally determining 3 one or more third masses or mass to charge ratios and one or more third ion mobility values, collision cross sections or interaction cross sections of at least some of the third ions, and experimentally determining one or more fourth masses or mass to charge ratios and one or more fourth ion mobility values, collision cross sections or interaction cross sections of at least some of the fourth ions. The first, second, third and/or fourth mass or mass to charge ratios and/or the first, second, third and/or fourth ion mobility values, collision cross sections or interaction cross sections are compared 4 in order to confirm the presence and/or absence of one or more reaction products of interest in the sample.

20 Claims, 1 Drawing Sheet

(56) References Cited

U.S. PATENT DOCUMENTS

| | | | |
|---|---|---|---|
| 8,242,442 | B2 | 8/2012 | Krueger et al. |
| 8,278,620 | B2 | 10/2012 | Schwartz et al. |
| 8,384,024 | B2 | 2/2013 | Miller et al. |
| 8,618,477 | B2 | 12/2013 | Krueger et al. |
| 2005/0048564 | A1* | 3/2005 | Emili ............... G01N 33/6818 435/7.1 |
| 2006/0234326 | A1* | 10/2006 | Cerda ............... C12Q 1/00 435/15 |
| 2007/0114382 | A1 | 5/2007 | Clemmer et al. |
| 2010/0108877 | A1 | 5/2010 | Wu et al. |
| 2010/0127166 | A1 | 5/2010 | Krueger et al. |
| 2010/0224770 | A1 | 9/2010 | Burns et al. |
| 2012/0171679 | A1* | 7/2012 | Ecker ............... C12Q 1/6813 435/6.12 |
| 2013/0009053 | A1 | 1/2013 | Wu |
| 2013/0218478 | A1 | 8/2013 | Campuzano et al. |
| 2016/0054264 | A1 | 2/2016 | Carver et al. |

FOREIGN PATENT DOCUMENTS

| | | |
|---|---|---|
| WO | 2004012231 | 2/2004 |
| WO | 2006114580 | 11/2006 |

OTHER PUBLICATIONS

Green et al., "Modification of Ion Mobility Separation Using Volatile Organic Dopants on a Quadrupole-Ion Mobility-Orthogonal Time-Of-Flight Mass Spectrometer", Proceedings 59th ASMS, 2011.

Williams et al., "Use of Ion Mobility Mass Spectrometry and a Collision Cross-Section Algorithm to Study an Organometallic Ruthenium Anticancer Complex and its Adducts with a DNA Oligonucleotide", RCM, p. 3563-3569, Jun. 2009.

Cris Lapthorn et al., "Ion mobility spectrometry-mass spectrometry (IMS-MS) of small molecules: Separating and assigning structures to ions", Mass spectrometry reviews, vol. 32, No. 1, pp. 43-71, Aug. 2012.

Alexandre A. Shvartsburg et al., "An exact hard-spheres scattering model for the mobilities of polyatomic ions", Chemical Physics Letters, vol. 261, No. 1, pp. 86-91, Oct. 1996.

Roberto Fernández-Maestre et al., "Buffer gas modifiers effect resolution in ion mobility spectrometry through selective ion-molecule clustering reactions", Rapid Communications in Mass Spectrometry, vol. 26, No. 19, pp. 2211-2223, Sep. 2012.

Roberto Fernández-Maestre et al., "Using a buffer gas modifier to change separation selectivity in ion mobility spectrometry", International journal of mass spectrometry, vol. 298, No. 1-3, pp. 2-9, Dec. 2010.

Matthew F. Bush et al., "Collision cross sections of proteins and their complexes: a calibration framework and database for gas-phase structural biology", Analytical Chemistry, vol. 82, No. 22, pp. 9557-9565, Oct. 2010.

Tom W. Knapman et al., "Considerations in experimental and theoretical collision cross-section measurements of small molecules using travelling wave ion mobility spectrometry-mass spectrometry", International Journal of Mass Spectrometry, vol. 298, No. 1-3, pp. 17-23, Dec. 2010.

* cited by examiner

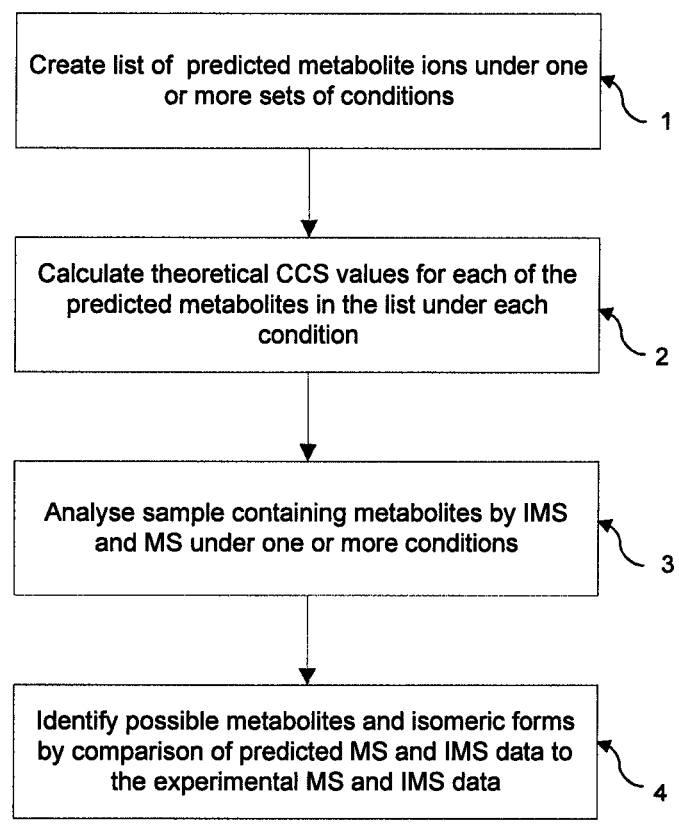

USING THEORETICAL COLLISION CROSS SECTION ("CCS") IN SAMPLE IDENTIFICATION

CROSS REFERENCE TO RELATED APPLICATIONS

This application is the National Stage of International Application No. PCT/GB2015/050702, filed 10 Mar. 2015 which claims priority from and the benefit of United Kingdom patent application No. 1404195.8 filed on 10 Mar. 2014 and European patent application No. 14158643.8 filed on 10 Mar. 2014. The entire contents of these applications are incorporated herein by reference.

FIELD OF THE INVENTION

The present invention relates generally to mass spectrometry and in particular to methods of mass spectrometry and mass spectrometers.

BACKGROUND

In metabolite identification ("ID") experiments a drug may be administered to an organism and some period of time later a biological sample may be taken and analysed for the presence and quantity of metabolites of that drug.

Biotransformation of target drugs in the body is part of the natural elimination process that generally produces inactive metabolites in a process of detoxification. However, biotransformation can sometimes lead to metabolites which are themselves toxic (bioactivation). Pharmaceutical industries are mandated by regulatory agencies to identify all metabolites.

Identification of metabolites is therefore an important and often time consuming step in the development of pharmaceutical compounds.

It is common to predict common metabolomic products of pharmaceutical compounds in a particular biological system using in silico calculation and bio-chemical knowledge.

For example, metabolites from oxidation, reduction, hydrolysis, cyclization and decyclization of a parent drug may be predicted given a drug structure and knowledge of the biological system. Conjugation such as methylation, suphonation, acetylation, glucuronidation, glutathione conjugation and glycine conjugation are also commonly expected and possible metabolites may be hypothesized.

In known mass spectrometric metabolite identification experiments, the structure, elemental composition and hence accurate mass of each expected or proposed metabolite is used to identify these compounds if they exist in the biological sample analysed.

However, it may not be possible to identify the isomeric forms of a particular metabolite from mass to charge ratio alone. In addition, because of the complexity of the biological sample matrix, mass interferences can lead to misidentification.

WO 2011/128703 (Micromass) discloses a method of identifying a sample compound that involves calculating a theoretical collision cross-section value for each of two or more known compounds, measuring a collision cross-section value for the sample compound, and comparing the measured value with the theoretical values to identify which of the two or more known compounds the sample compound most closely resembles.

It is desired to provide an improved method of mass spectrometry.

SUMMARY

According to an aspect there is provided a method of mass spectrometry comprising:

predicting one or more first reaction products which may result from subjecting an analyte to one or more reactions of interest;

calculating one or more first masses or mass to charge ratios and one or more first ion mobility values, collision cross sections or interaction cross sections of at least some first reaction product ions which may be generated from the one or more first reaction products under first conditions;

calculating one or more second masses or mass to charge ratios and one or more second ion mobility values, collision cross sections or interaction cross sections of at least some second reaction product ions which may be generated from the one or more first reaction products under second different conditions;

generating third ions from a sample under the first conditions;

generating fourth ions from the sample under the second conditions;

experimentally determining one or more third masses or mass to charge ratios and one or more third ion mobility values, collision cross sections or interaction cross sections of at least some of the third ions;

experimentally determining one or more fourth masses or mass to charge ratios and one or more fourth ion mobility values, collision cross sections or interaction cross sections of at least some of the fourth ions; and comparing the first, second, third and/or fourth mass or mass to charge ratios and/or the first, second, third and/or fourth ion mobility values, collision cross sections or interaction cross sections in order to confirm the presence and/or absence of one or more reaction products of interest in the sample.

An embodiment relates to the use of theoretically calculated Collision Cross Section ("CCS") of common expected reaction products in a reaction of interest, such as metabolites, to confirm the presence of a particular reaction product, such as a particular metabolite or metabolite isomer.

The embodiment adds specificity to compound identification analysis, such as metabolite identification analysis, in order to reduce the probability of misidentification of reaction products or metabolites.

While it is known to use ion mobility in combination with mass spectrometry to increase the peak capacity of the analytical instrumentation and to remove some interference which would otherwise lead to misidentification of reaction products or metabolites, in conventional approaches the collision cross section of the reaction products or metabolites is not generally determined and is not therefore used as an extra identification criteria.

The embodiment allows identification and quantification of the isomeric forms of each reaction product or metabolite which cannot be determined from mass to charge ratio alone. Although it is known that isomers may be separated by Ion Mobility Spectrometry ("IMS"), the presence of a particular isomer cannot be confirmed without theoretical calculation of its Collision Cross Section. The only alternative would be to synthesize each possible reaction product or metabolite or isomer and produce experimental results to compare with the results from the biological sample. This is impractical in most laboratories.

Furthermore, according to an embodiment and in contrast with e.g. WO 2011/128703 (Micromass), ions are generated from the sample under first conditions and second different conditions, and/or ions generated from the sample are analysed under first experimental conditions and under second different experimental conditions. The determined values of mass, mass to charge ratio, ion mobility, collision cross section and/or interaction cross section are compared in order to confirm the presence and/or absence of one or more reaction products of interest in the sample.

The embodiment accordingly allows more specificity to confirm the presence of reaction products of interest, reduces false positive identification, and increases the accuracy of the identification.

It will be apparent, therefore, that an improved method of mass spectrometry is provided.

According to an embodiment, the method further comprises:

determining a first mass or mass to charge ratio difference between the one or more first masses or mass to charge ratios and the one or more second masses or mass to charge ratios;

determining a second mass or mass to charge ratio difference between the one or more third masses or mass to charge ratios and the one or more fourth masses or mass to charge ratios;

comparing the first and second mass or mass to charge ratio differences in order to confirm the presence and/or absence of one or more reaction products of interest in the sample.

According to an embodiment, the method further comprises:

determining a first ion mobility, collision cross section or interaction cross section difference between the one or more first ion mobility values, collision cross sections or interaction cross sections and the one or more second ion mobility values, collision cross sections or interaction cross sections;

determining a second ion mobility, collision cross section or interaction cross section difference between the one or more third ion mobility values, collision cross sections or interaction cross sections and the one or more fourth ion mobility values, collision cross sections or interaction cross sections;

comparing the first and second ion mobility, collision cross section or interaction cross section differences in order to confirm the presence and/or absence of one or more reaction products of interest in the sample.

According to an embodiment, the method comprises:

calculating one or more first additional physico-chemical or other properties of at least some of the first ions;

calculating one or more second additional physico-chemical or other properties of at least some of second first ions;

experimentally determining one or more third additional physico-chemical or other properties of at least some of the third ions;

experimentally determining one or more fourth additional physico-chemical or other properties of at least some of the fourth ions; and comparing the first, second, third and/or fourth additional physico-chemical or other properties in order to confirm the presence and/or absence of one or more reaction products of interest in the sample.

According to an embodiment, the method further comprises:

determining a first additional physico-chemical or other property difference between the one or more first additional physico-chemical or other properties and the one or more second additional physico-chemical or other properties;

determining a second additional physico-chemical or other property difference between the one or more third additional physico-chemical or other properties and the one or more fourth additional physico-chemical or other properties;

comparing the first and second additional physico-chemical or other property differences in order to confirm the presence and/or absence of one or more reaction products of interest in the sample.

According to an embodiment, the one or more additional physico-chemical or other properties comprise isotope ratio pattern, peak shape, peak width, peak skew, number of peaks, and/or peak kurtosis.

According to an embodiment:

the step of calculating the one or more first masses or mass to charge ratios comprises calculating a first mass or mass to charge ratio of at least some of the first ions which would result from determining the first mass or mass to charge ratio under first experimental conditions, and calculating a first mass or mass to charge ratio of at least some of the first ions which would result from determining the first mass or mass to charge ratio under second different experimental conditions; and the step of experimentally determining the one or more third masses or mass to charge ratios comprises experimentally determining a third mass or mass to charge ratio of at least some of the third ions under the first experimental conditions, and experimentally determining a third mass or mass to charge ratio of at least some of the third ions under the second experimental conditions.

According to an embodiment:

the step of calculating the one or more second masses or mass to charge ratios comprises calculating a second mass or mass to charge ratio of at least some of the second ions which would result from determining the second mass or mass to charge ratio under first experimental conditions, and calculating a second mass or mass to charge ratio of at least some of the second ions which would result from determining the second mass or mass to charge ratio under second different experimental conditions; and the step of experimentally determining the one or more fourth masses or mass to charge ratios comprises experimentally determining a fourth mass or mass to charge ratio of at least some of the fourth ions under the first experimental conditions, and experimentally determining a fourth mass or mass to charge ratio of at least some of the fourth ions under the second experimental conditions.

According to an embodiment:

the step of calculating the one or more first ion mobility values, collision cross sections or interaction cross sections comprises calculating a first ion mobility value, collision cross section or interaction cross section of at least some of the first ions which would result from determining the first ion mobility value, collision cross section or interaction cross section under first experimental conditions, and calculating a first ion mobility value, collision cross section or interaction cross section of at least some of the first ions which would result from determining the first ion mobility value, collision cross section or interaction cross section under second different experimental conditions; and the step of experimentally determining the one or more third ion mobility values, collision cross sections or interaction cross sections comprises experimentally determining a third ion mobility value, collision cross section or interaction cross section of at least some of the third ions under the first experimental conditions, and experimentally determining a third ion mobility value, collision cross section or interaction cross section of at least some of the third ions under the second experimental conditions.

According to an embodiment:

the step of calculating the one or more second ion mobility values, collision cross sections or interaction cross sections comprises calculating a second ion mobility value, collision cross section or interaction cross section of at least some of the second ions which would result from determining the second ion mobility value, collision cross section or interaction cross section under first experimental conditions, and calculating a second ion mobility value, collision cross section or interaction cross section of at least some of the second ions which would result from determining the second ion mobility value, collision cross section or interaction cross section under second different experimental conditions; and the step of experimentally determining the one or more fourth ion mobility values, collision cross sections or interaction cross sections comprises experimentally determining a fourth ion mobility value, collision cross section or interaction cross section of at least some of the fourth ions under the first experimental conditions, and experimentally determining a fourth ion mobility value, collision cross section or interaction cross section of at least some of the fourth ions under the second experimental conditions.

According to another aspect there is provided a method of mass spectrometry comprising:

predicting one or more first reaction products which may result from subjecting an analyte to one or more reactions of interest;

calculating one or more masses or mass to charge ratios and one or more ion mobility values, collision cross sections or interaction cross sections of at least some corresponding reaction product ions under first experimental conditions;

calculating one or more masses or mass to charge ratios and one or more ion mobility values, collision cross sections or interaction cross sections of at least some of the reaction product ions under second different experimental conditions;

generating ions from a sample;

experimentally determining one or more masses or mass to charge ratios and one or more ion mobility values, collision cross sections or interaction cross sections of at least some of the generated ions under the first experimental conditions;

experimentally determining one or more masses or mass to charge ratios and one or more ion mobility values, collision cross sections or interaction cross sections of at least some of the generated ions under the second different experimental conditions; and comparing the calculated and experimentally determined masses or mass to charge ratios and/or the calculated and experimentally determined ion mobility values, collision cross sections or interaction cross sections in order to confirm the presence and/or absence of one or more reaction products of interest in the sample.

According to an embodiment, the method further comprises:

determining a first mass or mass to charge ratio difference between the one or more masses or mass to charge ratios calculated under the first experimental conditions and the one or more masses or mass to charge ratios calculated under the second experimental conditions;

determining a second mass or mass to charge ratio difference between the one or more masses or mass to charge ratios determined under the first experimental conditions and the one or more masses or mass to charge ratios determined under the second experimental conditions; and comparing the first and second mass or mass to charge ratio differences in order to confirm the presence and/or absence of one or more reaction products of interest in the sample.

According to an embodiment, the method further comprises:

determining a first ion mobility, collision cross section or interaction cross section difference between the one or more ion mobility values, collision cross sections or interaction cross sections calculated under the first experimental conditions and the one or more ion mobility values, collision cross sections or interaction cross sections calculated under the second experimental conditions;

determining a second ion mobility value, collision cross section or interaction cross section difference between the one or more ion mobility values, collision cross sections or interaction cross sections determined under the first experimental conditions and the one or more ion mobility values, collision cross sections or interaction cross sections determined under the second experimental conditions; and comparing the first and second ion mobility, collision cross section or interaction cross section differences in order to confirm the presence and/or absence of one or more reaction products of interest in the sample.

According to an embodiment, the method comprises:

calculating one or more additional physico-chemical or other properties of at least some of the reaction product ions under the first experimental conditions;

calculating one or more additional physico-chemical or other properties of at least some of the reaction product ions under the second different experimental conditions;

experimentally determining one or more additional physico-chemical or other properties of at least some of the generated ions under the first experimental conditions;

experimentally determining one or more additional physico-chemical or other properties of at least some of the generated ions under the second different experimental conditions; and comparing the calculated and experimentally determined additional physico-chemical or other properties in order to confirm the presence and/or absence of one or more reaction products of interest in the sample.

According to an embodiment, the method further comprises:

determining a first additional physico-chemical or other property difference between the one or more additional physico-chemical or other properties calculated under the first experimental conditions and the one or more additional physico-chemical or other properties calculated under the second experimental conditions;

determining a second additional physico-chemical or other property difference between the one or more additional physico-chemical or other properties determined under the first experimental conditions and the one or more additional physico-chemical or other properties determined under the second experimental conditions; and comparing the first and second additional physico-chemical or other property differences in order to confirm the presence and/or absence of one or more reaction products of interest in the sample.

According to an embodiment, the one or more additional physico-chemical or other properties comprise isotope ratio pattern, peak shape, peak width, peak skew, number of peaks and/or peak kurtosis.

According to an embodiment:

the reaction product ions comprise first ions which may be generated from the one or more first reaction products under first conditions, and second ions which may be generated from the one or more first reaction products under second different conditions; and the step of generating the ions comprises generating third ions from the sample under the first conditions, and generating fourth ions from the sample under the second conditions.

According to an embodiment:

the step of experimentally determining one or more masses or mass to charge ratios and one or more ion mobility values, collision cross sections or interaction cross sections of at least some of the generated ions under the first and/or second experimental conditions comprises:

experimentally determining one or more third masses or mass to charge ratios and one or more third ion mobility values, collision cross sections or interaction cross sections of at least some of the third ions; and experimentally determining one or more fourth masses or mass to charge ratios and one or more fourth ion mobility values, collision cross sections or interaction cross sections of at least some of the fourth ions;

According to an embodiment:

the step of comparing the calculated and experimentally determined masses or mass to charge ratios and/or the calculated and experimentally determined ion mobility values, collision cross sections or interaction cross sections comprises:

comparing the first, second, third and/or fourth mass or mass to charge ratios and/or the first, second, third and/or fourth ion mobility values, collision cross sections or interaction cross sections in order to confirm the presence and/or absence of one or more reaction products of interest in the sample.

According to an embodiment, the one or more reactions comprise one or more biological and/or chemical reactions.

According to an embodiment, the one or more reactions comprise one or more biotransformation and/or metabolomic reactions.

According to an embodiment, the one or more reactions comprise one or more of: (i) oxidation; (ii) reduction; (iii) hydrolysis; (iv) cyclization; (v) decyclization; (vi) conjugation; (vii) methylation; (viii) suphonation; (ix) acetylation; (x) glucuronidation; (xi) glutathione conjugation; and/or (xii) glycine conjugation.

According to an embodiment, the one or more reaction products comprise one or more metabolites of the analyte.

According to an embodiment, the analyte comprises a pharmaceutical compound.

According to an embodiment, the one or more reactions comprise one or more organic or catalytic reactions.

According to an embodiment, the sample comprises one or more second reaction products resulting from having subjected an analyte to one or more reactions.

According to an embodiment:

the reaction product ions comprise ions and/or parent or precursor ions and/or isomeric ions and/or fragment, product or adduct ions and/or conformer ions which may be generated directly or indirectly from the one or more first reaction products; and/or the generated ions comprise ions and/or parent or precursor ions and/or isomeric ions and/or fragment, product or adduct ions and/or conformer ions generated directly or indirectly from the sample.

According to an embodiment:

the first conditions comprise one or more first pre-ionisation, ionisation or post-ionisation conditions; and the second different conditions comprise one or more second pre-ionisation, ionisation or post-ionisation conditions second ions.

According to an embodiment, the first or second conditions are selected from the group consisting of:

(i) the composition and/or concentration of a salt, dopant, derivatisation agent, reagent, shift reagent, supercharging reagent or charge reduction reagent which is added to a liquid sample prior to ionisation;

(ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;

(iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation; and (iv) the composition and/or concentration of dopant ions, derivatisation ions, reagent ions, supercharging reagent ions or charge reduction reagent ions which are arranged to interact or react with analyte ions after ionisation.

According to an embodiment, the first or second conditions are selected from the group consisting of: (i) a condition that affects a charge state of the analyte ions; (ii) a condition that affects an energy level of the analyte ions; (iii) a condition that affects the kinetic energy of the analyte ions; (iv) a condition that affects an activation energy of the analyte ions; and (v) a condition that affects the conformational form or nature of the analyte ions.

According to an embodiment, the first or second conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

According to an embodiment, the first or second conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation; (viii) one or more electromagnetic radiation, microwave radiation or laser irradiation conditions; (ix) subjecting ions to fragmentation or reaction; and (ix) one or more fragmentation or reaction conditions.

According to an embodiment, the step of experimentally determining the one or more masses or mass to charge ratios comprises mass analysing the ions.

According to an embodiment, the step of experimentally determining the one or more ion mobility values, collision cross sections or interaction cross sections comprises passing at least some of the ions through an ion mobility separation device.

According to an embodiment, the first or second experimental conditions are selected from the group consisting of: (i) a voltage applied to an ion-optical component; (ii) a route taken by analyte ions through a portion of the mass spectrometer; (iii) the transit time of analyte ions through a portion of the mass spectrometer; (iv) one or more pressures within the mass spectrometer; (v) one or more temperatures within the mass spectrometer; (vi) the composition of a gas within the mass spectrometer; and (vii) the strength of an electric filed within the mass spectrometer.

According to an embodiment, the first or second experimental conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length travelled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

According to an embodiment, the step of calculating the one or more masses or mass to charge ratios of the reaction product ions comprises calculating an elemental composition and/or exact mass of one of more of the reaction product ions.

According to an embodiment, the step of calculating the one or more ion mobility values, collision cross sections or interaction cross sections of the reaction product ions comprises:

calculating a three dimensional structure of one or more of the reaction product ions; and calculating one or more of the one or more ion mobility values, collision cross sections or interaction cross sections using the three dimensional structure.

According to an embodiment, the step of calculating the one or more ion mobility values, collision cross sections or interaction cross sections of ions comprises calculating the effects of electronic interactions of the ions with a polar or polarisable ion mobility separation or buffer gas.

According to an aspect there is provided a mass spectrometer comprising:

a control system arranged and adapted:

(i) to predict one or more first reaction products which may result from subjecting an analyte to one or more reactions of interest;

(ii) to calculate one or more first masses or mass to charge ratios and one or more first ion mobility values, collision cross sections or interaction cross sections of at least some first reaction product ions which may be generated from the one or more first reaction products under first conditions; and (iii) to calculate one or more second masses or mass to charge ratios and one or more second ion mobility values, collision cross sections or interaction cross sections of at least some second reaction product ions which may be generated from the one or more first reaction products under second different conditions; and apparatus arranged and adapted:

(i) to generate third ions from a sample under the first conditions;

(ii) to generate fourth ions from the sample under the second conditions;

(iii) to experimentally determine one or more third masses or mass to charge ratios and one or more third ion mobility values, collision cross sections or interaction cross sections of at least some of the third ions; and (iv) experimentally determine one or more fourth masses or mass to charge ratios and one or more fourth ion mobility values, collision cross sections or interaction cross sections of at least some of the fourth ions;

wherein the control system is further arranged and adapted to compare the first, second, third and/or fourth mass or mass to charge ratios and/or the first, second, third and/or fourth ion mobility values, collision cross sections or interaction cross sections in order to confirm the presence and/or absence of one or more reaction products of interest in the sample.

According to an aspect there is provided a mass spectrometer comprising:

a control system arranged and adapted:

(i) to predict one or more first reaction products which may result from subjecting an analyte to one or more reactions of interest;

(ii) to calculate one or more masses or mass to charge ratios and one or more ion mobility values, collision cross sections or interaction cross sections of at least some corresponding reaction product ions under first experimental conditions; and (iii) to calculate one or more masses or mass to charge ratios and one or more ion mobility values, collision cross sections or interaction cross sections of at least some of the reaction product ions under second different experimental conditions; and apparatus arranged and adapted:

(i) to generate ions from a sample;

(ii) to experimentally determine one or more masses or mass to charge ratios and one or more ion mobility values, collision cross sections or interaction cross sections of at least some of the generated ions under the first experimental conditions; and (iii) to experimentally determine one or more masses or mass to charge ratios and one or more ion mobility values, collision cross sections or interaction cross sections of at least some of the generated ions under the second different experimental conditions;

wherein the control system is further arranged and adapted to compare the calculated and experimentally determined masses or mass to charge ratios and/or the calculated and experimentally determined ion mobility values, collision cross sections or interaction cross sections in order to confirm the presence and/or absence of one or more reaction products of interest in the sample.

According to an aspect there is provided a method of mass spectrometry comprising:

predicting one or more first reaction products which may result from subjecting an analyte to one or more reactions of interest;

calculating one or more first masses or mass to charge ratios and one or more first ion mobility values, collision cross sections or interaction cross sections of at least some corresponding first reaction product ions;

generating second ions from a sample;

experimentally determining one or more second masses or mass to charge ratios and one or more second ion mobility values, collision cross sections or interaction cross sections of at least some of the second ions; and comparing the first and second mass or mass to charge ratios and/or the first and second ion mobility values, collision cross sections or interaction cross sections in order to confirm the presence and/or absence of one or more reaction products of interest in the sample.

According to an aspect there is provided a mass spectrometer comprising:

a control system arranged and adapted:

(i) to predict one or more first reaction products which may result from subjecting an analyte to one or more reactions of interest; and (ii) to calculate one or more first masses or mass to charge ratios and one or more first ion mobility values, collision cross sections or interaction cross sections of at least some corresponding first reaction product ions; and apparatus arranged and adapted:

(i) to generate second ions from a sample; and (ii) to experimentally determine one or more second masses or mass to charge ratios and one or more second ion mobility values, collision cross sections or interaction cross sections of at least some of the second ions;

wherein the control system is further arranged and adapted to compare the first and second mass or mass to charge ratios and/or the first and second ion mobility values, collision cross sections or interaction cross sections in order to confirm the presence and/or absence of one or more reaction products of interest in the sample.

According to an aspect there is provided a method of mass spectrometry comprising:

(a) for a known pharmaceutical compound generating a list of expected metabolite ions including adducts, modifications, isomers and calculating the elemental composition, exact mass and proposing possible characteristic fragment ions;

(b) calculating, in silico, possible three dimensional structures for each of the proposed metabolite ions including isomeric structures and proposed fragment ions;

(c) calculating, in silico, the collision cross section or interaction cross section for each of the said structures;

(d) administering the pharmaceutical compound to an organism and obtaining a sample containing metabolites of the pharmaceutical compound;

(e) analysing a sample from the organism by Ion Mobility Spectrometry ("IMS") and mass spectrometry; and (f) identifying possible metabolites and isomeric forms in the sample using a combination of exact mass measurement, isotope ratios, fragment ions and theoretically calculated collision cross section.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer may further comprise a device arranged and adapted to supply an AC or RF voltage to the electrodes. The AC or RF voltage may has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector may selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector may selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which:

FIG. 1 shows a flow diagram illustrating an embodiment.

DETAILED DESCRIPTION

An embodiment is directed to a method in which one or more first reaction products which may result from subjecting an analyte to one or more reactions of interest are predicted. Given a proposed compound identity, probable three dimensional gas phase structures may be calculated for expected gas phase ions. Molecular mechanics and quantum chemistry modelling approaches may be employed to do this. Commercially available software such as Gaussian (www.gaussian.com) may be used to do this.

Once structures are proposed, the collision cross section is may calculated using, for example, software such as MobCal from Indiana University. Reference is made to: A. A. Shvartsburg and M. F. Jarrold, An Exact Hard Spheres Scattering Model for the Mobilities of Polyatomic Ions, Chem. Phys. Lett. 1996, 261, 86-91.

The effect on apparent Collision Cross Section of long range electronic interactions between ions and polar or polarisable molecules in an ion mobility drift media (buffer gas) may be taken into account within these calculations, e.g. to, in effect, calculate an interaction cross section.

According to an embodiment, one or more masses or mass to charge ratios and one or more ion mobility values, collision cross sections or interaction cross sections (i.e. drift time, ion mobility drift time, ion mobility, or differential ion mobility), optionally together with additional physico-chemical or other properties of the ions (such as for example, isotope ratio pattern, mass to charge ratio or ion mobility peak shape, mass to charge ratio or ion mobility peak width, skew of a mass to charge ratio or ion mobility peak, number of mass to charge ratio or ion mobility peaks and/or kurtosis of a mass to charge ratio or ion mobility peak) may be calculated for reaction product ions by considering two or more different analytical conditions. The analytical conditions may comprise different pre-ionisation, ionisation and/or post-ionisation conditions and/or different experimental or measurement conditions.

According to the embodiment, ions are generated from a sample and analysed using the two or more selected analytical conditions, and mass to charge ratios, collision cross sections or interaction cross sections, and any additional physico-chemical or other properties of the ions, may be determined. The experimentally determined values and the calculated values are may compared in order to confirm the presence and/or absence of one or more reaction products of interest in the sample.

FIG. 1 shows a flow diagram illustrating an embodiment.

As a first step 1, potential metabolites are identified. Common bio-transformations are well documented and a list of proposed target metabolites is generated. This list includes, for example, isomeric forms of a given predicted metabolite and characteristic fragment ions.

To add more specificity to the identification, the sample is analysed more than once under different solution phase and/or gas phase conditions (i.e. under different pre-ionisation, ionisation and/or post-ionisation conditions) in order to change the nature of the metabolite ions and/or under different (experimental or measurement) conditions under which ions are analysed.

Depending on e.g. the facilities within a particular laboratory and the flexibility of the design of the ion source and inlet to the ion source, a range of different conditions may be investigated including the following preferred conditions. The following list of conditions is not exhaustive.

a. Different Solution and Gas Phase Chemistry Designed to Alter the Nature of the Gas Phase Ion Generated from the Analytes.

In embodiments using Electrospray ionization, addition of a salt solution into the analyte flow prior to ionization can allow the charge carrier, associated with the analyte ion, to be controlled or to produce known analyte ion adducts.

For example, in positive ion Electrospray, addition of formic acid results in predominantly protonated ions being formed $[M+nH]^{n+}$ wherein n is the number of charges. Addition of sodium chloride (NaCl) results in predominantly sodiated ions $[M+nNa]^{n+}$.

In general, adducts of the form $[M+nY]^{n+}$ may be formed by addition of a suitable soluble ionic salt, wherein Y=Na, K, Li, H, $NH_3$, etc.

In embodiments using negative ion mode, adducts may be formed in a similar manner. For example, adducts may be formed by addition of soluble salts to give $[M+X]^{-}$ wherein X=F, Cl, Br, I, $NO_3$, etc. In negative ion mode $[M-nH]^{-n}$ ions may be produced by addition of ammonium hydroxide for example.

Many more embodiments of differing solution phase chemistry are contemplated. In some embodiments more complex derivatising agents may be employed based on knowledge of the chemical reactivity of the analytes.

For example, in embodiments that use Gas Chromatography ("GC") Mass Spectrometry ("MS"), acylation, silylation, alkylation and esterification may be used, these being common derivatisation methods using commercially available derivatisation reagents. In embodiments that use liquid chromatography ("LC") MS, Schiffbase forming reagents, primary and secondary amines and chromopores for fluorometric detection may be used, these being commonly available reagents. In these embodiments, derivatisation may be performed offline prior to separation.

In some embodiments, derivatisation of the ionized analyte may be performed in the gas phase either prior to ion mobility separation or within an ion mobility separation device. This may be achieved, for example, by the addition of reactive neutral or charged species into an RF confined reaction cell which is may maintained at sub atmospheric pressure.

In an embodiment, supercharging and/or charge reduction may additionally or alternatively be used to predictably alter the nature of the ions formed from the analyte.

According to an embodiment, the charge state of an ion may be manipulated either in the solution phase prior to ionization and/or in the gas phase, may by supercharging and/or charge reduction techniques. For example, in embodiments that use Electrospray Ionisation ("ESI"), the addition of mNBA ("m-nitrobenzyl alcohol"), tetramethylene sulfone ("sulfolane") or dimethyl sulfoxide ("DMSO") can result in an increase in the intensity of higher charged ions.

In an embodiment, charge reduction of analyte ions may be performed, may using an atmospheric or sub-atmospheric neutralization chamber may employing corona discharge or ultraviolet UV radiation or another energy source to produce reagent ions, which may be caused to interact with the analyte ions resulting in a lowering of the analyte ions' charge state. In other embodiments, basic compounds such as triethylammonium bicarbonate or imidazole may be added in solution prior to ionization and/or basic molecules may be introduced in the gas phase may at atmospheric or sub-atmospheric pressure so as to interact with the analyte ions.

In embodiments that use different ionization techniques, such as Atmospheric Pressure Chemical Ionisation ("APCI"), sub-atmospheric pressure chemical ionization, Matrix Assisted Laser Desorption Ionisation ("MALDI"), etc., other reagents or methods of manipulating the chemical nature of the analyte ions can be used.

In all of these embodiments the nature of the metabolite ions produced is predictable. In an embodiment, a single analyte may be manipulated to produce several different types of gas phase ions, may depending on the solution phase or gas phase chemistry available.

In an embodiment, solution or gas phase Hydrogen Deuterium Exchange ("HDX") may be employed. After Hydrogen Deuterium Exchange the mass to charge ratio of a metabolite ion and its isotope ratios will reflect the number of exchangeable hydrogen atoms on the molecule. This can give extra information and confirmation or rejection of possible metabolites identified in the sample. According to an embodiment, other reactions may be considered and used.

According to an embodiment, altering the charge carrier or charge state of ions can lead to significant changes in gas phase structure and hence collision cross section and so can cause compound specific shifts in ion mobility drift time and measured cross section. According to an embodiment, the electronic structure of a gas phase ion may be altered by changing the nature of the long range electronic interactions between the ion and the polarisable or polar drift media.

According to the preferred embodiment, a number of different alternative experiments may be contemplated giving rise to a number of different forms of the same metabolite ion. The expected or predicted metabolite ion species may be theoretically modelled and the theoretical ion mobility behaviour examined to confirm the presence or identity of this metabolite.

b. Different IMS Drift Gas Compositions

The choice of ion mobility separation drift media can dramatically affect separation by ion mobility separation. According to an embodiment, a polarisable drift gas, buffer gas or drift media may containing gas phase neutrals with a permanent dipole moment may be used to selectively change the separation of different analyte ions or isomer ions of an analyte. According to an embodiment, a selection of different drift gas compositions is made and the predicted effect on the analyte ions mobility is may investigated by theoretical Collision Cross Section calculation. Depending on the electronic structure of the analyte ions, ion mobility separation may be superior in one drift gas compared to another.

c. Different Pre-IMS or Intra-IMS Activation Energy

According to an embodiment, activation of an ion, e.g. to raise the internal temperature by an arbitrary or known amount, may be used to cause unfolding or transition between conformational states. In various embodiments, lasers or other energy sources may be used to excite ions before or during ion mobility separation.

Returning now to FIG. 1, in a second step 2, the theoretical Collision Cross Section values may be calculated for each of the predicted metabolites under each chosen pre-ionisation, ionisation, post-ionisation and/or experimental condition contemplated in the first step 1.

In a third step 3, the sample expected to contain at least some of the predicted metabolite ions is may analysed under one or more of the pre-ionisation, ionisation, post-ionisation, and/or experimental or measurement (e.g. mass spectrometry ("MS") and/or ion mobility separation) conditions chosen. In this step, mass spectrometry data, tandem mass spectrometry ("MS-MS") data or data using multiple stages of fragmentation or reaction ("MS$'''$") may be acquired.

In a fourth step 4, the presence of the metabolites proposed in the first step 1 may be confirmed using a combination of both the theoretical or predicted mass spectrometry ("MS") data (e.g. mass or mass to charge ratio, isotope pattern, isotope ratio(s), peak shape, peak width, peak skew, number of peaks, and/or peak kurtosis) and theoretical ion mobility data (e.g. ion mobility value, collision cross section and/or interaction cross section, peak shape, peak width, peak skew, number of peaks, and/or peak kurtosis).

Metabolites may be identified by comparing measured mass to charge ratio values to theoretical mass to charge ratio values, may be based on the predicted elemental composition. In addition, theoretical and experimental isotope ratios and/or theoretical and experimental product ion mass to charge ratio and intensity may be compared.

According to the preferred embodiment, in addition to this mass to charge ratio information, theoretical Collision Cross Section data may be compared with experimental data to add a higher degree of specificity and confidence to the identification. In this step the isomeric form of the metabolite may also be identified. This information is not available using mass to charge ratio alone.

As described above, to add more specificity to the identification, the sample may be analysed more than once under different conditions, such as solution phase or gas phase conditions that may change the nature of the metabolite ions formed, and/or under different experimental conditions that may change the nature of the IMS separation.

According to an embodiment, the sample may be analysed using two or more drift gas compositions and the experimental and theoretical shift in Collision Cross Section may compared. According to an embodiment, using a volatile polar dopant can give drift time shifts which are very specific to a given ion structure. According to an embodiment, theoretical calculations can give the magnitude of the expected shift in apparent Collision Cross Section and may be used to add specificity to metabolite identification.

Additionally or alternatively the metabolite may be modified by altering solution or gas phase chemistry. For example, in some embodiments the structure or Collision Cross Section of a protonated ion may be very different from the structure and Collision Cross Section of a sodiated ion or an ion with a different charge carrier or adduct or derivatisation modification. This change can be related to the stereochemistry or the electronic structure of the ion, and again the experimentally observed shift is may compared to the theoretically calculated shift to add specificity to the identification of the metabolite.

In an embodiment, a mass or mass to charge ratio difference and/or an ion mobility, collision cross section or interaction cross section difference between ions generated or measured under different analytical conditions may be used to confirm the presence and/or absence of one or more reaction products of interest in the sample. In particular, according to an embodiment the drift time difference of analyte ions which are caused to separate temporally in the presence of buffer gases which have different compositions are measured. This approach is particularly advantageous in that it is substantially more robust to changes in the conditions of the ion mobility separator than utilising an absolute drift time measurement. As a result, the approach according to this embodiment results in a significant improvement in precision and accuracy.

In an embodiment, one or more additional physico-chemical or other properties of the ions, such as an isotope pattern, isotope ratio or isotope ratio pattern, peak shape, peak width, peak skew, number of peaks, and/or peak kurtosis e.g. of a mass to charge ratio or ion mobility peak, may be calculated and experimentally determined, and used in order to confirm the presence and/or absence of one or more reaction products of interest in the sample, e.g. by comparing the calculated and experimentally determined values.

For example, the peak shape, width, etc. may be used, optionally as well as the mass to charge ratio, to add further specificity to the identification. It may be the case, for example, that a particular ion peak will split into two or more ions peaks under the second different conditions, or a shoulder or asymmetry etc. could appear. This could be due, for example, to the existence of a protomer, etc. and/or the existence of a different structure (e.g. collision cross section) and/or different electronic interactions with a (polar or polarisable) buffer gas.

In an embodiment, properties of one or more experimentally determined ion peaks, such as a width, skew or kurtosis, may be determined, e.g. using a peak shape fitting. The corresponding theoretical values may be calculated, e.g. by factoring in the device parameters and conditions (resolution, etc.) into the calculations, may so as to determine one or more expected peak shapes.

Although the above embodiment has been described in terms of identifying metabolites, the same procedure may be applied to different types of analysis where the starting material is known and product ions may be proposed.

For example, in organic synthesis or re-synthesis, the starting materials and target structure is known and structures possible impurities formed in the reaction processes may be hypothesized. In an embodiment, the theoretical cross sections of these possible products is calculated and used to confirm the presence of these compounds, may in the manner of the embodiments discussed above.

Another embodiment is catalytic processes which have known starting materials and proposed products which may be confirmed by theoretical Collision Cross Section calculation, may in the manner of the embodiments discussed above. Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
predicting one or more first reaction products which may result from subjecting an analyte to one or more reactions of interest;
calculating one or more first masses or mass to charge ratios and one or more first ion mobility values, collision cross sections or interaction cross sections of at least some first reaction product ions which may be generated from said one or more first reaction products under first conditions;
calculating one or more second masses or mass to charge ratios and one or more second ion mobility values, collision cross sections or interaction cross sections of at least some second reaction product ions which may be generated from said one or more first reaction products under second different conditions;
generating third ions from a sample under said first conditions;
generating fourth ions from said sample under said second conditions;
experimentally determining one or more third masses or mass to charge ratios and one or more third ion mobility values, collision cross sections or interaction cross sections of at least some of said third ions;
experimentally determining one or more fourth masses or mass to charge ratios and one or more fourth ion mobility values, collision cross sections or interaction cross sections of at least some of said fourth ions; and
comparing said first, second, third and/or fourth masses or mass to charge ratios and/or said first, second, third and/or fourth ion mobility values, collision cross sections or interaction cross sections in order to confirm the presence and/or absence of one or more reaction products of interest in said sample.

2. A method as claimed in claim 1, further comprising:
determining a first mass or mass to charge ratio difference between said one or more first masses or mass to charge ratios and said one or more second masses or mass to charge ratios;
determining a second mass or mass to charge ratio difference between said one or more third masses or mass to charge ratios and said one or more fourth masses or mass to charge ratios;
comparing said first and second mass or mass to charge ratio differences in order to confirm the presence and/or absence of one or more reaction products of interest in said sample.

3. A method as claimed in claim 1, further comprising:
determining a first ion mobility, collision cross section or interaction cross section difference between said one or more first ion mobility values, collision cross sections or interaction cross sections and said one or more second ion mobility values, collision cross sections or interaction cross sections;
determining a second ion mobility, collision cross section or interaction cross section difference between said one or more third ion mobility values, collision cross sections or interaction cross sections and said one or more fourth ion mobility values, collision cross sections or interaction cross sections;

comparing said first and second ion mobility, collision cross section or interaction cross section differences in order to confirm the presence and/or absence of one or more reaction products of interest in said sample.

4. A method as claimed in claim 1, wherein said method comprises:

calculating one or more first additional physico-chemical or other properties of at least some of said first ions;

calculating one or more second additional physico-chemical or other properties of at least some of said second ions;

experimentally determining one or more third additional physico-chemical or other properties of at least some of said third ions;

experimentally determining one or more fourth additional physico-chemical or other properties of at least some of said fourth ions; and comparing said first, second, third and/or fourth additional physico-chemical or other properties in order to confirm the presence and/or absence of one or more reaction products of interest in said sample.

5. A method as claimed in claim 4, wherein said one or more additional physico-chemical or other properties comprise isotope pattern, isotope ratio, peak shape, peak width, peak skew, number of peaks, and/or peak kurtosis.

6. A method as claimed in claim 1, wherein:

said step of calculating said one or more first masses or mass to charge ratios comprises calculating a first mass or mass to charge ratio of at least some of said first ions which would result from determining said first mass or mass to charge ratio under first experimental conditions, and calculating a first mass or mass to charge ratio of at least some of said first ions which would result from determining said first mass or mass to charge ratio under second different experimental conditions;

said step of experimentally determining said one or more third masses or mass to charge ratios comprises experimentally determining a third mass or mass to charge ratio of at least some of said third ions under said first experimental conditions, and experimentally determining a third mass or mass to charge ratio of at least some of said third ions under said second experimental conditions;

said step of calculating said one or more second masses or mass to charge ratios comprises calculating a second mass or mass to charge ratio of at least some of said second ions which would result from determining said second mass or mass to charge ratio under first experimental conditions, and calculating a second mass or mass to charge ratio of at least some of said second ions which would result from determining said second mass or mass to charge ratio under second different experimental conditions; and said step of experimentally determining said one or more fourth masses or mass to charge ratios comprises experimentally determining a fourth mass or mass to charge ratio of at least some of said fourth ions under said first experimental conditions, and experimentally determining a fourth mass or mass to charge ratio of at least some of said fourth ions under said second experimental conditions.

7. A method as claimed in claim 6, wherein said first or second experimental conditions are selected from the group consisting of: (i) a voltage applied to an ion-optical component; (ii) a route taken by analyte ions through a portion of said mass spectrometer; (iii) the transit time of analyte ions through a portion of said mass spectrometer; (iv) one or more pressures within said mass spectrometer; (v) one or more temperatures within said mass spectrometer; (vi) the composition of a gas within said mass spectrometer; and (vii) the strength of an electric filed within said mass spectrometer.

8. A method as claimed in claim 6, wherein said first or second experimental conditions are selected from the group consisting of: (i) the composition of an ion mobility separation or buffer gas; (ii) the composition of one or more additives, one or more dopants and/or one or more reagents added to an ion mobility separation or buffer gas; (iii) the flow rate and/or direction of an ion mobility separation or buffer gas; (iv) the pressure or number density of an ion mobility separation or buffer gas; (v) the temperature within an ion mobility separation device; (vi) the strength of an electric field within an ion mobility separation device; (vii) the path length travelled by ions within an ion mobility separation device; (viii) the residence time of ions within an ion mobility separation device; (ix) the initial width of an ion pulse introduced into an ion mobility separation device; and (x) the speed, amplitude or repeat pattern of a travelling DC wave within an ion mobility separation device.

9. A method as claimed in claim 1, wherein:

said step of calculating said one or more first ion mobility values, collision cross sections or interaction cross sections comprises calculating a first ion mobility value, collision cross section or interaction cross section of at least some of said first ions which would result from determining said first ion mobility value, collision cross section or interaction cross section under first experimental conditions, and calculating a first ion mobility value, collision cross section or interaction cross section of at least some of said first ions which would result from determining said first ion mobility value, collision cross section or interaction cross section under second different experimental conditions;

said step of experimentally determining said one or more third ion mobility values, collision cross sections or interaction cross sections comprises experimentally determining a third ion mobility value, collision cross section or interaction cross section of at least some of said third ions under said first experimental conditions, and experimentally determining a third ion mobility value, collision cross section or interaction cross section of at least some of said third ions under said second experimental conditions;

said step of calculating said one or more second ion mobility values, collision cross sections or interaction cross sections comprises calculating a second ion mobility value, collision cross section or interaction cross section of at least some of said second ions which would result from determining said second ion mobility value, collision cross section or interaction cross section under first experimental conditions, and calculating a second ion mobility value, collision cross section or interaction cross section of at least some of said second ions which would result from determining said second ion mobility value, collision cross section or interaction cross section under second different experimental conditions; and said step of experimentally determining said one or more fourth ion mobility values collision cross sections or interaction cross sections comprises experimentally determining a fourth ion mobility value, collision cross section or interaction cross section of at least some of said fourth ions under said first experimental conditions, and experimentally determining a fourth ion mobility value, collision cross section or interaction cross section of at least some of said fourth ions under said second experimental conditions.

10. A method as claimed in claim 1, wherein said one or more reactions comprise one or more biotransformation and/or metabolomic reactions, and/or one or more organic or catalytic reactions.

11. A method as claimed in claim 1, wherein:
said first conditions comprise one or more first pre-ionisation, ionisation or post-ionisation conditions; and
said second different conditions comprise one or more second pre-ionisation, ionisation or post-ionisation conditions second ions.

12. A method as claimed in claim 1, wherein said first or second conditions are selected from the group consisting of:
(i) the composition and/or concentration of a salt, dopant, derivatisation agent, reagent, shift reagent, supercharging reagent or charge reduction reagent which is added to a liquid sample prior to ionisation;
(ii) the composition and/or concentration of a neutral gas, dopant gas, derivatisation agent gas, reagent gas, shift reagent gas, supercharging reagent gas or charge reduction reagent gas which is added to a gaseous or vapour phase sample prior to ionisation;
(iii) the composition and/or concentration of a neutral gas, reactive gas, dopant gas, derivatisation agent, reagent gas, shift reagent gas, supercharging reagent gas or charge reduction reagent gas which is arranged to interact or react with analyte ions after ionisation; and
(iv) the composition and/or concentration of dopant ions, derivatisation ions, reagent ions, supercharging reagent ions or charge reduction reagent ions which are arranged to interact or react with analyte ions after ionisation.

13. A method as claimed in claim 12, wherein said first or second conditions are selected from the group consisting of: (i) a condition that affects a charge state of said analyte ions; (ii) a condition that affects an energy level of said analyte ions; (iii) a condition that affects the kinetic energy of said analyte ions; (iv) a condition that affects an activation energy of said analyte ions; and (v) a condition that affects the conformational form or nature of said analyte ions.

14. A method as claimed in claim 1, wherein said first or second conditions are selected from the group consisting of: (i) an ionisation condition of an ion source; (ii) the type of ion source used to ionise a sample; (iii) a voltage setting of an ion source; (iv) an ionisation polarity of ions being generated by an ion source; (v) a flow rate of sample supplied to an ion source; (vi) one or more liquid chromatography conditions of a liquid chromatography system; (vii) a composition of a liquid chromatography solution or solvent; and (viii) a liquid chromatography flow rate.

15. A method as claimed in claim 1, wherein said first or second conditions are selected from the group consisting of: (i) subjecting ions to hydrogen deuterium exchange; (ii) one or more hydrogen deuterium exchange conditions; (iii) subjecting ions to activation, photo-activation, dissociation or photo-dissociation; (iv) one or more dissociation, photo-dissociation, activation, and/or photo-activation conditions; (v) subjecting ions to heating or RF heating; (vi) one or more heating or RF heating conditions; (vii) subjecting ions to electromagnetic radiation, microwave radiation or laser irradiation; (viii) one or more electromagnetic radiation, microwave radiation or laser irradiation conditions; (ix) subjecting ions to fragmentation or reaction; and (ix) one or more fragmentation or reaction conditions.

16. A method as claimed in claim 1, wherein said step of calculating said one or more masses or mass to charge ratios of said reaction product ions comprises calculating an elemental composition and/or exact mass of one of more of said reaction product ions.

17. A method as claimed in claim 1, wherein said step of calculating said one or more ion mobility values, collision cross sections or interaction cross sections of said reaction product ions comprises:
calculating a three dimensional structure of one or more of said reaction product ions; and
calculating one or more of said one or more ion mobility values, collision cross sections or interaction cross sections using said three dimensional structure.

18. A method as claimed in claim 1, wherein said step of calculating said one or more ion mobility values, collision cross sections or interaction cross sections of ions comprises calculating the effects of electronic interactions of said ions with a polar or polarisable ion mobility separation or buffer gas.

19. A mass spectrometer comprising:
a control system arranged and adapted:
(i) to predict one or more first reaction products which may result from subjecting an analyte to one or more reactions of interest;
(ii) to calculate one or more first masses or mass to charge ratios and one or more first ion mobility values, collision cross sections or interaction cross sections of at least some first reaction product ions which may be generated from said one or more first reaction products under first conditions; and
(iii) to calculate one or more second masses or mass to charge ratios and one or more second ion mobility values, collision cross sections or interaction cross sections of at least some second reaction product ions which may be generated from said one or more first reaction products under second different conditions; and
apparatus arranged and adapted:
(i) to generate third ions from a sample under said first conditions;
(ii) to generate fourth ions from said sample under said second conditions;
(iii) to experimentally determine one or more third masses or mass to charge ratios and one or more third ion mobility values, collision cross sections or interaction cross sections of at least some of said third ions; and
(iv) to experimentally determine one or more fourth masses or mass to charge ratios and one or more fourth ion mobility values, collision cross sections or interaction cross sections of at least some of said fourth ions;
wherein said control system is further arranged and adapted to compare said first, second, third and/or fourth masses or mass to charge ratios and/or said first, second, third and/or fourth ion mobility values, collision cross sections or interaction cross sections in order to confirm the presence and/or absence of one or more reaction products of interest in said sample.

20. A method of mass spectrometry comprising:
predicting one or more first reaction products which may result from subjecting an analyte to one or more reactions of interest;
calculating one or more masses or mass to charge ratios and one or more ion mobility values, collision cross sections or interaction cross sections of at least some corresponding reaction product ions under first experimental conditions;

calculating one or more masses or mass to charge ratios and one or more ion mobility values, collision cross sections or interaction cross sections of at least some of said reaction product ions under second different experimental conditions;

generating ions from a sample;

experimentally determining one or more masses or mass to charge ratios and one or more ion mobility values, collision cross sections or interaction cross sections of at least some of said generated ions under said first experimental conditions;

experimentally determining one or more masses or mass to charge ratios and one or more ion mobility values, collision cross sections or interaction cross sections of at least some of said generated ions under said second different experimental conditions; and comparing said calculated and experimentally determined masses or mass to charge ratios and/or said calculated and experimentally determined ion mobility values, collision cross sections or interaction cross sections in order to confirm the presence and/or absence of one or more reaction products of interest in said sample.

* * * * *